United States Patent [19]

Barker

[11] Plant 4,226

[45] Mar. 21, 1978

[54] POTENTILLA

[75] Inventor: David Alan Barker, Much Hadham, England

[73] Assignee: Monrovia Nursery Company, Azusa, Calif.

[21] Appl. No.: 780,664

[22] Filed: Mar. 23, 1977

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Edmond F. Shanahan

[57] ABSTRACT

An ornamental, flowering shrub of the genus *Potentilla fruticosa,* having as its most important novel characteristic the ability to produce flowers which are red in color, a color not heretofore known in this genus. The seasonal development pattern of the new plant is later than that of other Potentilla varieties; both new leaves and flowers appear later in the spring than on other Potentilla, and last longer in the fall; however, very dry weather conditions cause red flowers to fade to a reddish-yellow, but the same flower becomes red again after rain. Another distinguishing characteristic is the foliage, which is a brighter green than in other Potentilla; and grows with more density, and more dwarf size than the seedling relatives.

2 Drawing Figures

DESCRIPTION

This invention relates to a new variety of *Potentilla fruticosa,* having a red flower, bright green foliage, and other characteristics novel to Potentillas.

The new plant was invented by Dr. David Alan Barker, who discovered it as a chance seedling, in the year 1972, in the garden of his home at "Hopleys", Much Hadham, Herts, England. Since its discovery in 1972, the plant has been reproduced asexually by means of cuttings, and found to produce consistently and true, with all of the cutting plants achieving first quality standards of the novel characteristics of the cultivar. The plant does not reproduce true from seed.

Neither seed parent nor pollen parent are known with any certainty; but it appears probable that the plant is a chance seedling of Potentilla "Tangerine", "Sunset", or "Daydawn", (all non-patented varieties), which, however, are readily recognizable as different from the new plant, particularly by their flowers, which are in the yellow, rather than the red range of color.

Like other Potentillas, the new plant requires a temperate, rather than a dry warm climate; and like other Potentillas, the leaves are alternate pinnate or palmate, and the flowers have the characteristic bracted calyx, five petals, and a fruit consisting of many small achenes heaped on a dry receptacle.

The accompanying drawing comprises two color photographs showing the plant in color, and showing the flowering of the plant both in bud and full bloom.

Throughout the following specification, colors are specified by reference to the Royal Horticultural Society Colour Chart.

BUD

The buds are indistinguishable, before flowering, from the yellow buds of the probable seedling parents. Before the calyx breaks, the bud is typical of Potentillas in size and structure, but the outside yellow petals have an occasional red streak. The inside petals are uniformly red, under suitableclimatic conditions.

BLOOM

The outstanding novelty of the new plant is the red coloring of the flowers (except when subject to unusually dry weather). The newly opened flower, given adequate moisture, appears with petals of R.H.S. Colour Chart Red Group 44B, the color is uniform and appears immediately upon opening.

When the flower is fully opened, its typical size is about one inch. Its five petals have an upper surface color which may change from R.H.S. Colour Chart Red Group 44B to R.H.S. Colour Chart, Orange/Red Group 33A. The petals have an undersurface yellow color, R.H.S. Colour Chart, Yellow/Orange Group 16D.

The flowers grow through many summer and fall stages depending upon the weather. In continual heat and drought, the flower colors fade rapidly nearly to yellow, but after rain, the red color reappears with a few days. The red flower production is particularly good during May to early June, and in the autumn season when night temperatures are cool. When the summer weather is dry, the red flower may fade from the colors above given to an Orange/Yellow color above noted; but the identical flower, if left on the plant, may regain its red color (Orange/Red Group 33A), with lower temperatures and more moisture.

FOLIAGE

The fully developed leaves are palmate, and typical of Potentillas. However, they are distinguishable by their bright matte finish, with an upper side color, R.H.S. Colour Chart, Green Group 137B, and an underside color of R.H.S. Colour Chart, Greyed Green Group 191A.

The leaf structure is generally typical of, and indistinguishable from, the leaves of the probable seedling Potentilla plants, but are of a distinctively brighter green color as specified above.

GROWTH

The shrub exhibits a low-growing compact habit with spreading branches, although the eventual dimensions of the mature plants are not yet known, present growth rates indicate a probable mature height of 2 to 2½ feet, and a probable mature spread of 3½ to 4 feet. The growth is dense, and the plant functions well as a ground cover.

I claim:

1. A new and distinct variety of Potentilla, substantially as described and illustrated herein, and capable of producing a red flower, and having the other distinguishing features that the foliage is brighter green, and appears in lower more compact growth than appears in related Potentillas.

* * * * *

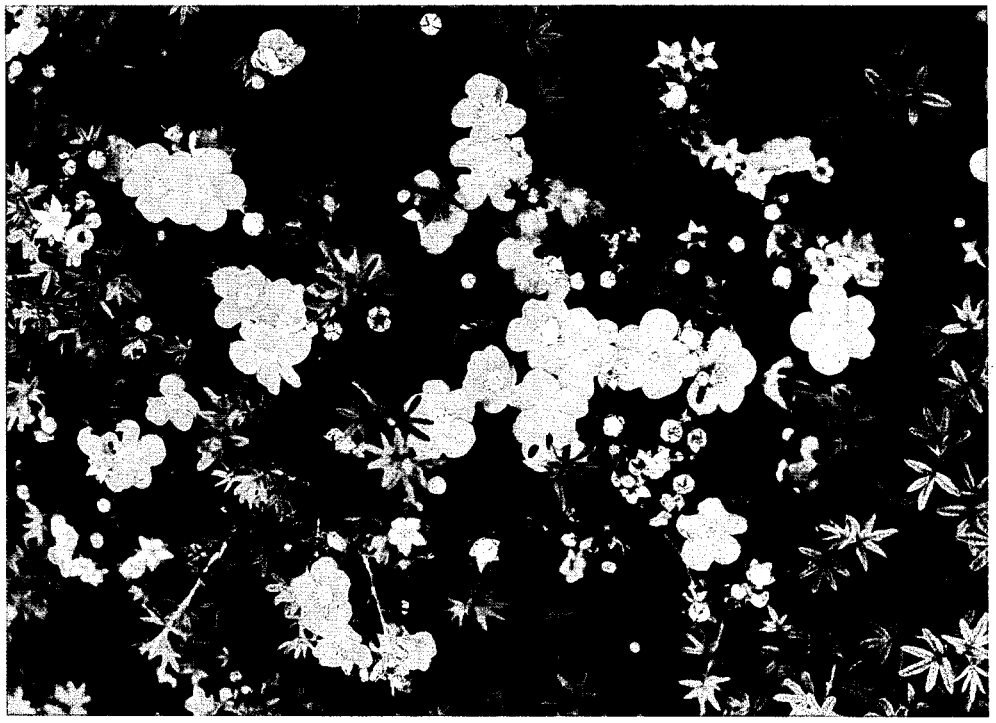
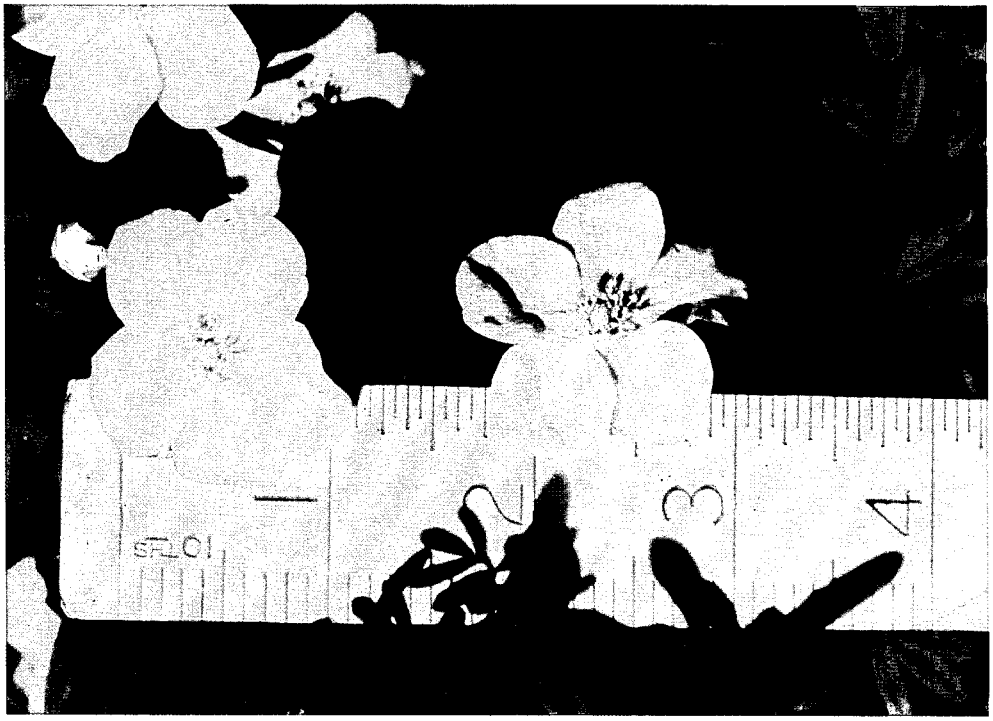
3
4